US00PP19306P2

(12) United States Plant Patent
Hawks

(10) Patent No.: US PP19,306 P2
(45) Date of Patent: Oct. 7, 2008

(54) ***CHRYSOGONUM* PLANT NAMED 'QUINN'S GOLD'**

(50) Latin Name: *Chrysogonum virginianum*
Varietal Denomination: Quinn's Gold

(76) Inventor: Kimberly T. Hawks, 2056 Crawford Dairy Rd., Chapel Hill, NC (US) 27516

( * ) Notice: Subject to any disclaimer, the term of this patent is extended or adjusted under 35 U.S.C. 154(b) by 0 days.

(21) Appl. No.: 11/906,656

(22) Filed: Oct. 4, 2007

(51) Int. Cl.
*A01H 5/00* (2006.01)

(52) U.S. Cl. ..... Plt./373
(58) Field of Classification Search ..... Plt./373
See application file for complete search history.

*Primary Examiner*—Annette H Para
*Assistant Examiner*—S. B. McCormick-Ewoldt
(74) *Attorney, Agent, or Firm*—Penny J. Aguirre

(57) ABSTRACT

A new cultivar of *Chrysogonum virginianum,* 'Quinn's Gold', characterized by its flowers that emerge gold in color and change with maturity to yellow and creamy white imparting the appearance of multicolored flowers, its long blooming habit, its vigorous growth habit, its ease of propagation, its drought tolerance and its hardiness in at least U.S.D.A. Zones 5 to 9.

2 Drawing Sheets

Botanical classification: *Chrysogonum virginianum.*
Variety denomination: 'Quinn's Gold'.

BACKGROUND OF THE INVENTION

The present invention relates to a new and distinct cultivar of *Chrysogonum virginianum* and will be referred to hereafter by its cultivar name, 'Quinn's Gold'. 'Quinn's Gold' represents a new green and gold, an herbaceous perennial herb grown for use as a groundcover and in perennial borders.

The new cultivar, 'Quinn's Gold', was discovered by the inventor as a naturally occurring whole plant mutation in a cultivated garden in Pittsboro, N.C. in June of 1998. 'Quinn's Gold' was found in a groundcover planting of unnamed *Chrysogonum virginianum* plants and arose from open pollination of these plants.

Asexual reproduction of the new cultivar was first accomplished by division in June of 1998 by the inventor in Chapel Hill, N.C. Propagation by division and stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Quinn's Gold' as a unique cultivar of *Chrysogonum.*

1. 'Quinn's Gold' exhibits flowers that open gold in color and change color with maturity from gold to yellow and finally to a creamy white color.
2. Plants of 'Quinn's Gold' are multicolored in bloom as the flower are continuously produced and are present in various stage of floral development.
3. 'Quinn's Gold' is long blooming; blooming from early spring until frost.
4. 'Quinn's Gold' has a vigorous growth habit and is readily propagated by stem cuttings.
5. 'Quinn's Gold' is drought tolerant.

6. 'Quinn's Gold' is cold hardy at least in U.S.D.A. Zones 5 to 9.

The new *Chrysogonum* is unique in comparison to other cultivars and species of *Chrysogonum* known to the inventor. The parent plants, unnamed plants of *Chrysogonum virginianum,* produce flowers that are gold throughout development and do not lighten to yellow and creamy white as observed with 'Quinn's Gold'.

The only cultivars known to the inventor are cultivars of *Chrysogonum virginianum* var. *virginianum* that produce more upright stems and a habit that forms discreet clumps rather than the groundcover habit typical of *Chrysogonum virginianum* and 'Quinn's Gold'. None of these cultivars produce flowers that change in color like 'Quinn's Gold'. These cultivars include 'Pierre' (not patented), which is a compact selection and 'Mark Viette' (not patented), which is fast growing and has abundant large flowers.

BRIEF DESCRIPTION OF THE DRAWINGS

The plants and plant parts in the accompanying color photographs were taken of a one year-old plant grown in outdoors in a trial bed in New Hope, Minn.

Figure 1:
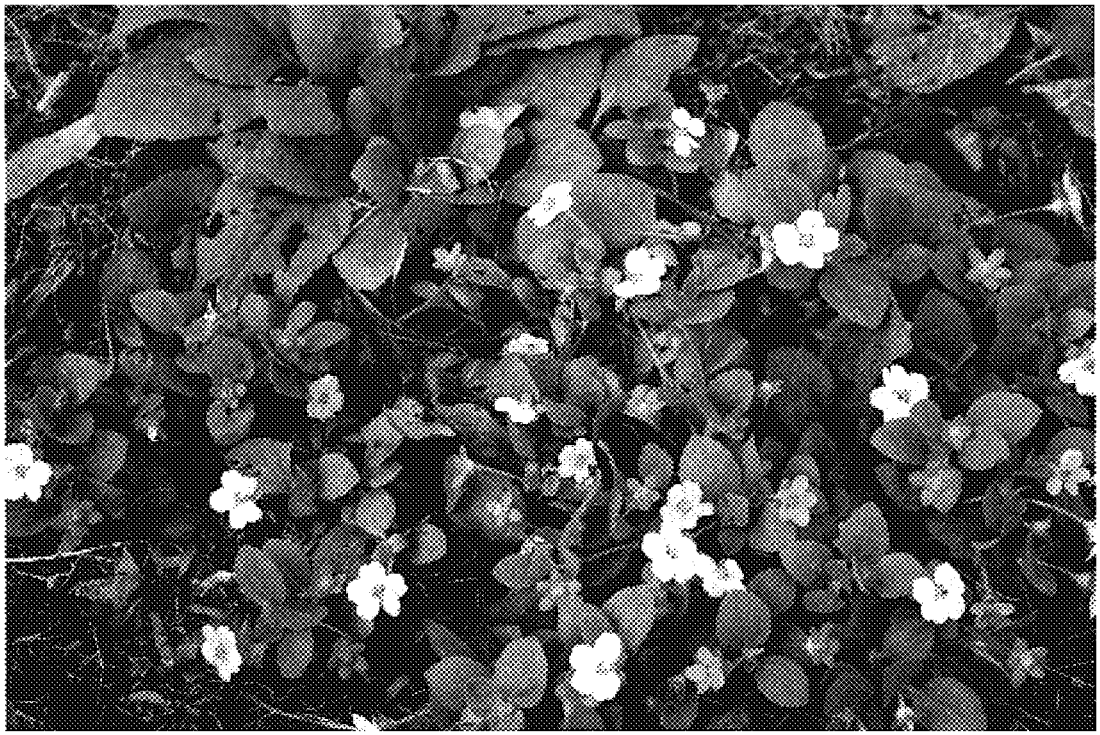
FIG. 1 provides an overall view of 'Quinn's Gold' in bloom and illustrates plant habit.
Figure 2:
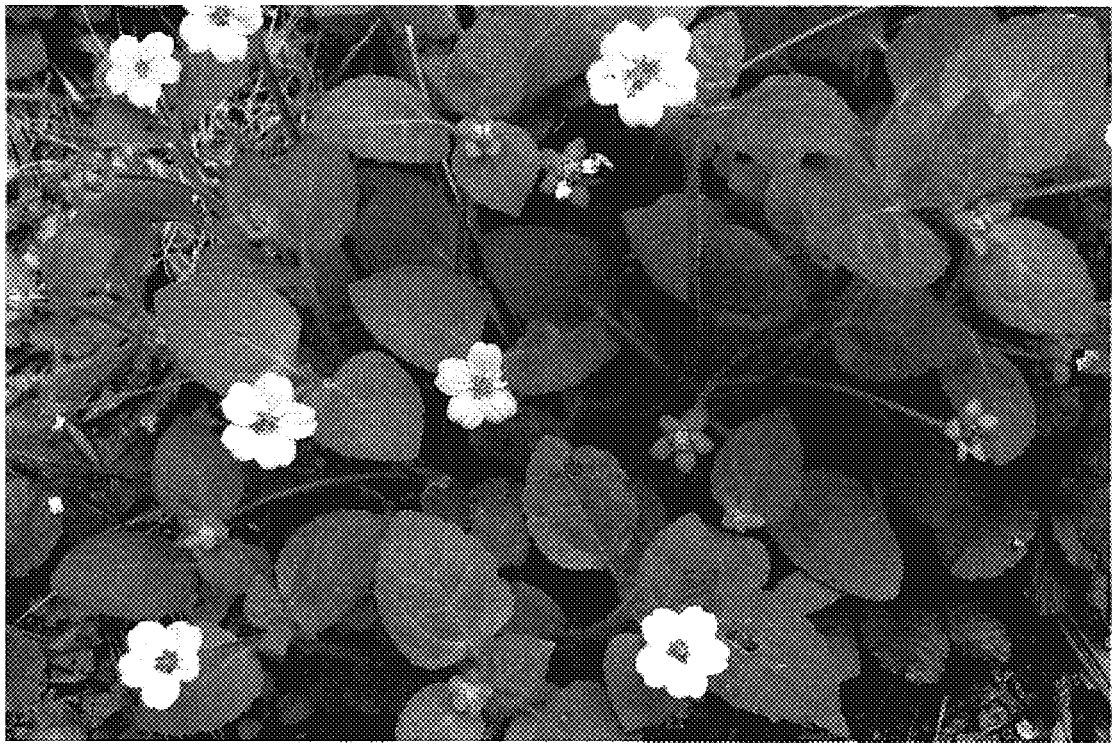
FIG. 2 provides a close-up view of the flowers in various stages of development.

The colors in the photographs are as close as possible with the photographic and printing technology utilized. The color values cited in the detailed botanical description more accurately describe the colors of the new *Chrysogonum.*

BOTANICAL DESCRIPTION OF THE PLANT

The following is a detailed description of a one-year old plant the new cultivar as grown outdoors in a trial garden in New Hope, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Long-blooming; from mid spring until frost in Minnesota and North Carolina.

*Plant type.*—Herbaceous perennial herb.

*Plant habit.*—Flowering stems emerge from a basal rosette and are prostrate in habit, suitable as a groundcover.

*Height and spread.*—Reaches up to 10 cm in height and reaches about 40 cm in width.

*Hardiness.*—At least in U.S.D.A. Zones 5 to 9.

*Culture.*—Grows best in well-drained, moderately rich to lean soils in full sun to dappled shade and its drought tolerant.

*Diseases and pests.*—No susceptibility or resistance to diseases or pests has been observed.

*Root description.*—Fleshy.

*Growth rate.*—Vigorous.

*Propagation.*—Stem cuttings and stem division.

Stem description:

*Shape.*—Slightly oval, solid.

*Stem color.*—145A with some areas suffused with 176B on upper surface.

*Stem size.*—Average of 3 mm in diameter; initially short and later branching and elongating to about 25 cm.

*Stem surface.*—Pubescent with numerous white hairs about 2 mm in length.

*Stem number.*—Average of 6 branched flowering stems.

*Internode length.*—Average of 5 cm, with some nodes having two branches per node.

*Branching.*—Typically an average of 2 branches per stem with 3 to 4 tertiary branches.

Foliage description:

*Leaf shape.*—Ovate.

*Leaf division.*—Simple.

*Leaf base.*—Attenuate.

*Leaf arrangement.*—Opposite.

*Leaf apex.*—Broadly acute.

*Leaf venation.*—Primarily pinnate, not prominent except for basal portion of mid rib; 147D in color.

*Leaf margins.*—Dentate, ciliate.

*Leaf attachment.*—Petiolate.

*Leaf size.*—Basal leaves; average of 8 cm in length and 5 cm in width, stem leaves; average of 3 cm in length and 2 cm in width.

*Leaf color.*—Newly formed upper surface; 137B, newly formed lower surface; 138A, mature leaf upper surface; 137B, mature leaf lower surface; 138B.

*Leaf surface.*—Upper surface dull and lower pubescent with short hairs on margins.

*Petioles.*—About 4 mm in length and 2 mm in width on flowering stems and about 4.5 cm in length and 4 mm in width on basal leaves with leafy margins, 145D in color.

Flower description:

*Type.*—Capitulum, ray florets around the head margin with disk florets in the center, forming a radiant head, present on terminal and axillary nodes of flowering stems, emerging from the onset of stem elongation.

*Capitulum number.*—About 40 per branched flowering stem.

*Lastingness of inflorescence.*—About 2 weeks until senescence of ray flowers, disk florets and bracts are persistent.

*Capitulum size.*—Matures to about 1 cm in depth and 1.5 cm in diameter, disk size is about 4 cm in diameter.

*Fragrance.*—None detected.

*Phyllaries.*—10, arranged in 2 series, outer series; about 7 mm in length and 4 mm in width, fused at base, broadly acute apex, broadly oblanceolate in shape, color 138B on upper portion and 138D on lower portion on both surfaces, entire, ciliate margin and glabrous hairy surface, lower portion chaffy, inner series; about 4 mm in length and 2.5 mm in width, 138D in color, chaffy.

*Buds.*—Campanulate, 7 mm in depth and 1.5 cm in diameter, phyllary are 138A on upper surface and 138B on lower surface, ray florets are upright, 2 mm in height, 1.5 mm in width and 14A in color, disk florets are barely visible and 144D in color.

*Peduncle.*—Typically 3 cm in length and 1.2 mm in diameter, 145A in color, texture is glabrous and rough with abundant hairs.

*Ray florets* (*female*).—5, about 1 cm in length and 4 mm in width, petals; broadly oval in shape, emarginated apex, cuneate base, entire margin except apex, glabrous in texture, initially held upright about 70° from horizontal and become horizontal as they mature, color of upper and lower surface when opening; 14A, color changes to upper surface; 8D with shadings of 8A and 8B and lower surface; blending of 13A, 8A and 8B, color of upper surface when mature; 155B with a small marking of 8B at apex and base, color of lower surface when mature; blend of 11B and 11C.

*Disk flowers* (*male and female, or sterile*).—Numerous, about 20, tubular in shape, arranged spirally on a conical receptacle, about 4 mm in length and 1 mm in width, petals; 5, fused, tubular with acute apices, 14A in color, pistil extends 1.5 mm beyond apex, general disk color at opening 14A, changing to 2D then to a blend of 165A and 165D when ray florets drop.

Reproductive organs:

*Gynoecium.*—Pistil: 1, 3 mm in length and 0.7 mm in width, style; 0.7 mm in width and 2 mm in length, color 14A, stigma; bifid, each arm about 2 mm in length and 14A in color, ovary; about 3 mm in length and 2 mm in width, 138D in color, oval in shape.

*Androecium.*—Stamens; 5, fused, form a cylinder around style, 3 mm in length and 0.3 mm in width, dehisced longitudinally, 200A in color, filaments; 1 mm in length, 0.3 m in width, 153D in color, pollen; moderate in quantity and 14A in color.

It is claimed:

1. A new and distinct cultivar of *Chrysogonum* plant named 'Quinn's Gold' as herein illustrated and described.

* * * * *